United States Patent
Malhotra et al.

(10) Patent No.: US 12,090,163 B2
(45) Date of Patent: Sep. 17, 2024

(54) PHARMACEUTICAL COMPOSITIONS

(71) Applicant: CIPLA LIMITED, Mumbai (IN)

(72) Inventors: Geena Malhotra, Mumbai (IN); Kalpana Joshi, Thane (IN); Jeevan Ghosalkar, Dombivali (IN); Atul Daroi, Thane (IN); Siddharth Agrawal, Nagpur (IN)

(73) Assignee: CIPLA LIMITED, Mumbai (IN)

( * ) Notice: Subject to any disclaimer, the term of this patent is extended or adjusted under 35 U.S.C. 154(b) by 0 days.

(21) Appl. No.: 16/626,502

(22) PCT Filed: Jun. 29, 2018

(86) PCT No.: PCT/IN2018/050427
§ 371 (c)(1),
(2) Date: Dec. 24, 2019

(87) PCT Pub. No.: WO2019/003251
PCT Pub. Date: Jan. 3, 2019

(65) Prior Publication Data
US 2020/0113919 A1   Apr. 16, 2020

(30) Foreign Application Priority Data
Jun. 30, 2017   (IN) .............................. 201721023142

(51) Int. Cl.
*A61K 31/675* (2006.01)
*A61P 31/18* (2006.01)
*A61P 31/22* (2006.01)
*A61K 45/06* (2006.01)
*B82Y 5/00* (2011.01)

(52) U.S. Cl.
CPC ............ *A61K 31/675* (2013.01); *A61P 31/18* (2018.01); *A61P 31/22* (2018.01); *A61K 45/06* (2013.01); *B82Y 5/00* (2013.01)

(58) Field of Classification Search
CPC ... A61K 31/675; A61K 2300/00; A61P 31/12; A61P 31/18
USPC .......................................................... 514/80
See application file for complete search history.

(56) References Cited

U.S. PATENT DOCUMENTS

| 7,390,791 B2 | 6/2008 | Becker et al. |
| 9,227,990 B2 | 1/2016 | Phull et al. |

(Continued)

FOREIGN PATENT DOCUMENTS

| IN | 201721023142 | 6/2017 |
| WO | 2014068265 A1 | 5/2014 |
| WO | 2019003251 A1 | 1/2019 |

OTHER PUBLICATIONS

Ray et al. "Tenofovir alafenamide: A novel prodrug of tenofovir for the treatment of human immunodeficiency virus," Antiviral Research, 2016 vol. 125, pp. 63-70 (Year: 2016).*

(Continued)

*Primary Examiner* — San Ming R Hui
(74) *Attorney, Agent, or Firm* — Conley Rose, P.C.; Rodney B. Carroll

(57) ABSTRACT

The invention relates to pharmaceutical compositions comprising ((((((R)-1-(6-amino-9H-purin-9-yl)propan-2-yl)oxy)methyl)(phenoxy)phosphoryl)oxy)methyl pivalate or a pharmaceutically acceptable derivative thereof, optionally with an additional agent, methods of making them, and their use in medicine.

20 Claims, 2 Drawing Sheets

Inhibition of HIV-1 JV1083 replication in PBMC

(56) References Cited

U.S. PATENT DOCUMENTS

| | | | |
|---|---|---|---|
| 2010/0143301 A1* | 6/2010 | Desai | A61P 1/00 |
| | | | 424/85.7 |
| 2016/0199396 A1* | 7/2016 | Shahar | A61K 31/513 |
| | | | 424/474 |
| 2017/0044140 A1* | 2/2017 | Zhang | A61P 31/14 |

OTHER PUBLICATIONS

OARAC "Guidelines for the use of antiretroviral agents in HIV-1-infected Adults and adolescents," https://clinicalinfo.hiv.gov/sites/default/files/guidelines/documents/AdultandAdolescentGL.pdf (Year: 2017).*

Foreign communication from related application—International Search Report, PCT Application No. PCT/IN2018/050427, dated Oct. 4, 2018, 3 pages.

Foreign communication from related application—Written Opinion of the International Searching Authority, PCT Application No. PCT/IN2018/050427, dated Oct. 4, 2018, 5 pages.

Buckheit, Robert W., Jr. et al., "Characterization of an HIV-1 Isolate Displaying an Apparent Absence of Virion-Associated Reverse Transcriptase Activity," AIDS Research and Human Retroviruses, 1991, pp. 295-302, vol. 7, Mary Ann Liebert, Inc., Publishers.

Foreign communication from related application—International Preliminary Report on Patentability, PCT Application No. PCT/IN2018/050427, dated Dec. 31, 2019, 6 pages.

* cited by examiner

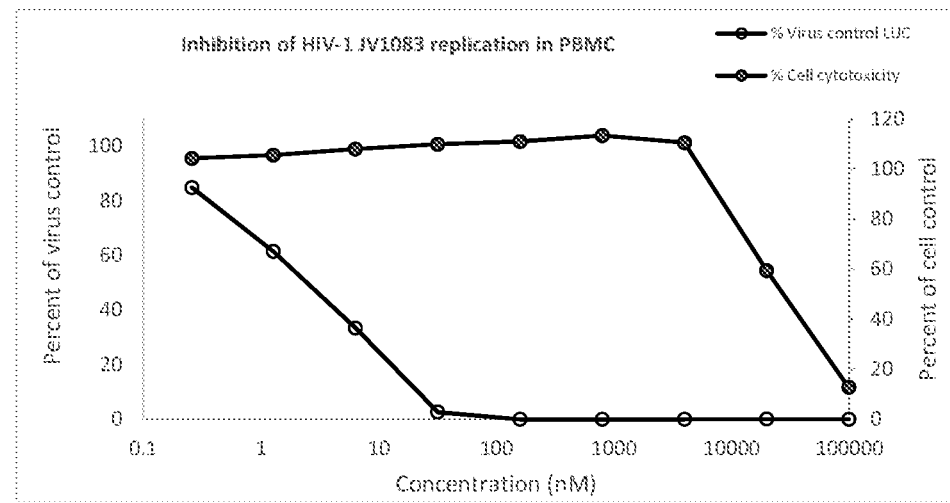
Figure 1: Inhibition of HIV-1 JV1083 replication in PBMC
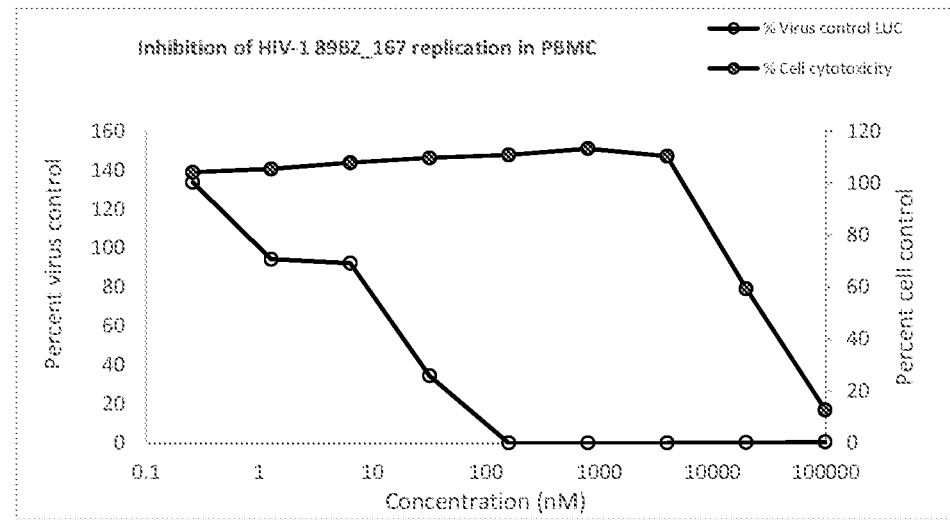
Figure 2: Inhibition of HIV-1 89BZ_167 replication in PBMC

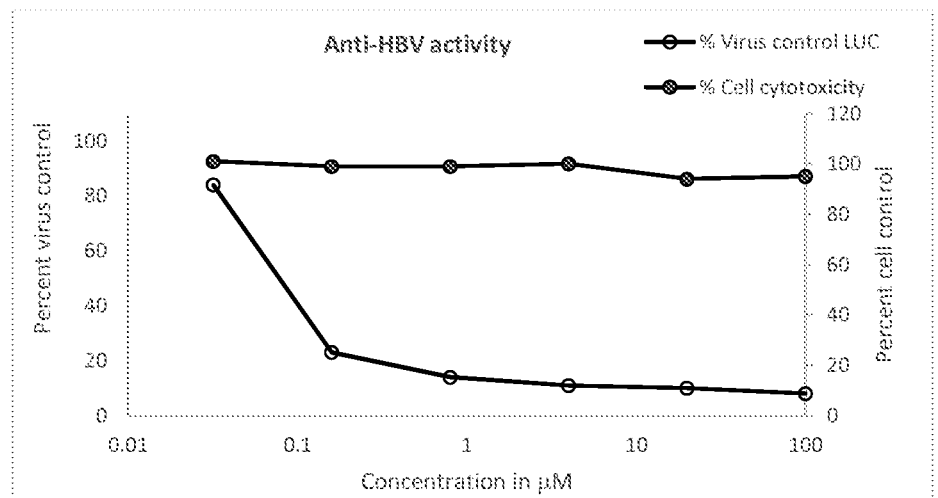
Figure 3: Anti-HBV activity
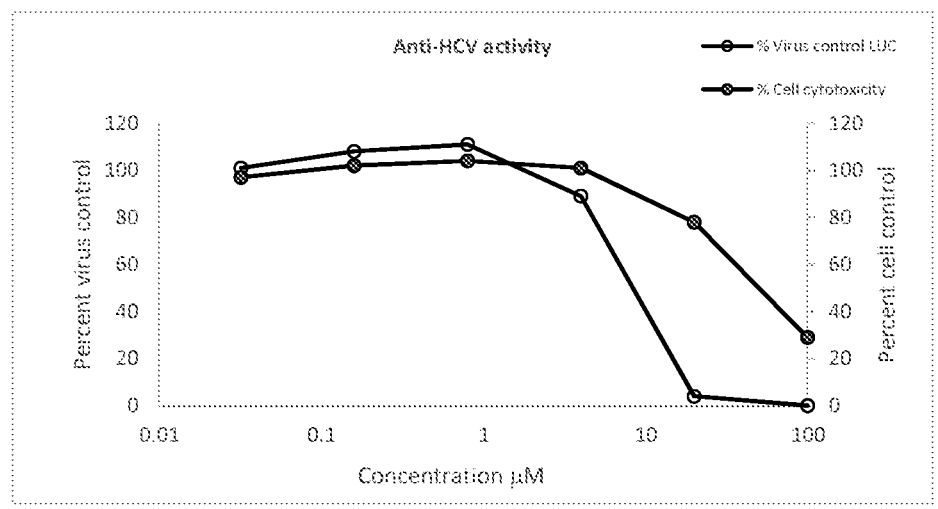
Figure 4: Anti-HCV activity

PHARMACEUTICAL COMPOSITIONS

CROSS REFERENCE TO RELATED APPLICATIONS

This application is a filing under 35 U.S.C. 371 of International Application No. PCT/IN2018/050427 filed Jun. 29, 2018, entitled "Pharmaceutical Compositions" which claims priority to Indian Patent Application Serial Number 201721023142 filed on Jun. 30, 2017, which applications are incorporated by reference herein in their entirety.

FIELD OF INVENTION

The present invention relates to pharmaceutical compositions comprising ((((((R)-1-(6-amino-9H-purin-9-yl)propan-2-yl)oxy)methyl)(phenoxy)phosphoryl)oxy)methyl pivalate or a pharmaceutically acceptable derivative thereof. The present invention also provides the manufacturing process thereof and use of the said compositions for the prevention, treatment or prophylaxis of diseases caused by viruses, specifically acquired immune deficiency syndrome or an HIV infection, Hepatitis B infection, or Hepatitis C infection.

BACKGROUND OF INVENTION

Human immunodeficiency virus, type 1 (HIV-1) infection is a life-threatening and serious disease of major public health significance, with approximately 36.7 million people infected worldwide (Joint United Nations Programme on HIV/AIDS (UNAIDS). Global report: UNAIDS report on the global AIDS epidemic, 2016).

Acquired Immune Deficiency Syndrome (AIDS) causes a gradual breakdown of the body's immune system as well as progressive deterioration of the central and peripheral nervous systems. Since its initial recognition in the early 1980s, AIDS has spread rapidly and has now reached epidemic proportions within a relatively limited segment of the population. Intensive research has led to the discovery of the responsible agent, human T-lymphotropic retrovirus 111 (HTLV-111) commonly referred to as the Human Immunodeficiency Virus or HIV.

Human Immunodeficiency Virus (HIV) is the etiological agent of Acquired Immune Deficiency Syndrome (AIDS) that has created a major health care problem not only in India but globally.

HIV is a member of the class of viruses known as retroviruses. The retroviral genome is composed of RNA, which is converted to DNA by reverse transcription. This retroviral DNA is then stably integrated into a host cell's chromosome and, employing the replicative process of that host cell, producing new retroviral particles and advancing the infection to other cells. HIV appears to have a particular affinity for the human T-4 lymphocyte cell which plays a vital role in the body's immune system. HIV infected WBCs lead to a decrease in WBC population. Eventually, the immune system is rendered inoperative and ineffective against various opportunistic diseases.

Tenofovir is a highly potent nucleotide analog reverse-transcriptase inhibitor which is widely used in the treatment of diseases caused by retroviruses, especially Acquired Immune Deficiency Syndrome or an HIV infection. Tenofovir {9-R-[(2-phosphonomethoxy)propyl]adenine}, an acyclic nucleotide analog of dAMP, is a potent in vitro and in vivo inhibitor of human immunodeficiency virus type 1 (HIV-1) replication. Tenofovir is sequentially phosphorylated in the cell by AMP kinase and nucleoside diphosphate kinase to the active species, tenofovir diphosphate, which acts as a competitive inhibitor of HIV-1 reverse transcriptase that terminates the growing viral DNA chain. The presence of a nonhydrolyzable phosphonic acid moiety in tenofovir circumvents an initial phosphorylation step that can be rate limiting for the activation of nucleoside analog inhibitors of HIV reverse transcriptase. Due to the presence of a phosphonate group, tenofovir is negatively charged at neutral pH, thus limiting its oral bioavailability.

Tenofovir disoproxil fumarate (TDF; VIREAD®), the first generation oral prodrug of tenofovir, has been extensively studied in clinical trials and has received marketing authorization in many countries as a once-daily tablet (300 mg) in combination with other antiretroviral agents for the treatment of HIV-1 infection.

U.S. Pat. No. 7,390,791 describes certain prodrugs of phosphonate nucleotide analogs that are useful in therapy. One such prodrug is Tenofovir alafenamide hemifumarate (TAF; Vemlidy®) which is an isopropylalaninyl phenyl ester prodrug of tenofovir.

Although TDF and TAF show desirable activities, the treatment cost and the potential for unwanted side effects can both increase as the required dose of a drug increases. Therefore, there is a need for methods and compositions that are useful for achieving an acceptable anti-viral effect using a reduced dose.

U.S. Pat. No. 9,227,990 (the content of which is incorporated by reference herein in its entirety) describe certain prodrugs of phosphonate nucleotide analogs that are useful in therapy. One such prodrug is ((((((R)-1-(6-amino-9H-purin-9-yl)propan-2-yl)oxy)methyl)(phenoxy)phosphoryl)oxy)methyl pivalate.

OBJECT OF THE INVENTION

An object of the present invention is to provide a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof; and one or more pharmaceutically acceptable excipients.

Another object of the present invention is to provide a process for preparing a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof and one or more pharmaceutically acceptable excipients.

Yet another object of the present invention is to provide a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof and at least one additional therapeutic agent; and one or more pharmaceutically acceptable excipients.

Yet another object of the present invention is to provide a use of ((((((R)-1-(6-amino-9H-purin-9-yl) propan-2-yl)oxy)methyl)(phenoxy)phosphoryl)oxy)methyl pivalate or a pharmaceutically acceptable derivative thereof for the prophylactic or therapeutic treatment of a viral infection in a human, wherein the viral infection is human immunodeficiency virus (HIV) or Hepatitis B infection (HBV) or Hepatitis C infection (HCV).

Yet another object of the present invention is to provide a method of prevention, treatment or prophylaxis of diseases caused by viruses, specifically Acquired Immune Deficiency Syndrome or an HIV infection or Hepatitis B infection or Hepatitis C infection, which method comprises administering a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof.

Yet another object of the present invention is to provide a method of prevention, treatment or prophylaxis of diseases caused by viruses, specifically Acquired Immune Deficiency Syndrome or an HIV infection or Hepatitis B infection or Hepatitis C infection, which method comprises administering a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof and at least one additional therapeutic agent.

SUMMARY OF THE INVENTION

According to an aspect of the present invention, there is provided a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof; and one or more pharmaceutically acceptable excipients.

According to another aspect of the present invention, there is provided a process for preparing a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof; and one or more pharmaceutically acceptable excipients.

According to yet another aspect of the present invention, there is provided a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof and at least one additional therapeutic agent; and one or more pharmaceutically acceptable excipients.

According to yet another aspect of the present invention, there is provided a use of ((((((R)-1-(6-amino-9H-purin-9-yl)propan-2-yl)oxy)methyl)(phenoxy)phosphoryl)oxy)methyl pivalate or a pharmaceutically acceptable derivative thereof for the prophylactic or therapeutic treatment of a viral infection in a human, wherein the viral infection is human immunodeficiency virus (HIV) or Hepatitis B infection (HBV) or Hepatitis C infection (HCV).

According to yet another aspect of the present invention, there is provided a method of prevention, treatment or prophylaxis of diseases caused by viruses, specifically Acquired Immune Deficiency Syndrome or an HIV infection or Hepatitis B infection or Hepatitis C infection, such method comprising administering a therapeutically effective amount of a pharmaceutical composition comprising ((((((R)-1-(6-amino-9H-purin-9-yl) propan-2-yl)oxy)methyl)(phenoxy)phosphoryl)oxy)methyl pivalate or a pharmaceutically acceptable derivative thereof to a patient in need thereof.

According to yet another aspect of the present invention, there is provided a method of prevention, treatment or prophylaxis of diseases caused by viruses, specifically Acquired Immune Deficiency Syndrome or an HIV infection or Hepatitis B infection or Hepatitis C infection, such method comprising administering a therapeutically effective amount of a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof and at least one additional therapeutic agent to a patient in need thereof.

BRIEF DESCRIPTION OF THE DRAWING

FIG. 1 represents in vitro efficacy of ((((((R)-1-(6-amino-9H-purin-9-yl)propan-2-yl)oxy)methyl)(phenoxy)phosphoryl)oxy)methyl pivalate fumarate against HIV-1 in fresh PBMCs by demonstrating inhibition of HIV-1 JV1083 replication in PBMC.

FIG. 2 represents in vitro efficacy of ((((((R)-1-(6-amino-9H-purin-9-yl)propan-2-yl)oxy)methyl)(phenoxy)phosphoryl)oxy)methyl pivalate fumarate against HIV-1 in fresh PBMCs by demonstrating inhibition of HIV-1 89BZ_167 replication in PBMC.

FIG. 3 represents in vitro efficacy of ((((((R)-1-(6-amino-9H-purin-9-yl)propan-2-yl)oxy)methyl)(phenoxy)phosphoryl)oxy)methyl pivalate fumarate against HBV cells in HepG2 cells demonstrating anti-HBV activity.

FIG. 4 represents in vitro efficacy of ((((((R)-1-(6-amino-9H-purin-9-yl)propan-2-yl)oxy)methyl)(phenoxy)phosphoryl)oxy)methyl pivalate fumarate against HCV using HCV replicon assay.

DETAILED DESCRIPTION OF THE INVENTION

U.S. Pat. No. 9,227,990 (the content of which is incorporated by reference herein in its entirety) describe certain prodrugs of phosphonate nucleotide analogs that are useful in therapy. One such prodrug is ((((((R)-1-(6-amino-9H-purin-9-yl)propan-2-yl)oxy)methyl)(phenoxy)phosphoryl)oxy)methyl pivalate (Formula 1).

Formula 1

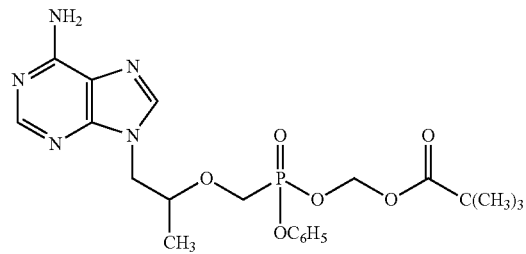

The present invention provides a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof; and one or more pharmaceutically acceptable excipients. The present invention also provides the manufacturing process thereof and use of the said compositions for the prevention, treatment or prophylaxis of diseases caused by viruses, specifically acquired immune deficiency syndrome or an HIV infection or Hepatitis B infection or Hepatitis C infection.

The term "((((((R)-1-(6-amino-9H-purin-9-yl)propan-2-yl)oxy)methyl)(phenoxy)phosphoryl)oxy)methyl pivalate" is used in broad sense to include not only "((((((R)-1-(6-amino-9H-purin-9-yl)propan-2-yl)oxy)methyl)(phenoxy)phosphoryl)oxy)methyl pivalate" per se but also its pharmaceutically acceptable derivatives thereof. Suitable pharmaceutically acceptable derivatives include pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

Preferably, ((((((R)-1-(6-amino-9H-purin-9-yl)propan-2-yl)oxy)methyl)(phenoxy)phosphoryl)oxy)methyl pivalate is in the form of a pharmaceutically acceptable acid addition salt thereof. Examples of the pharmaceutically acceptable acid addition salt of ((((((R)-1-(6-amino-9H-purin-9-yl)propan-2-yl)oxy)methyl)(phenoxy)phosphoryl)oxy)methyl pivalate include, but are not limited to, inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, succinic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Preferably, the acid is fumaric acid, tartaric acid or phosphoric acid. Fumaric acid is more preferably used, but the acid addition salt is not restricted thereto. Preferably, ((((((R)-1-(6-amino-9H-purin-9-yl)propan-2-yl)oxy)methyl)(phenoxy) phosphoryl) oxy)methyl pivalate is in the form of a fumarate salt.

In one embodiment, there is provided a pharmaceutical composition comprising ((((((R)-1-(6-amino-9H-purin-9-yl)propan-2-yl)oxy)methyl)(phenoxy)phosphoryl)oxy)methyl pivalate or a pharmaceutically acceptable derivative thereof; and one or more pharmaceutically acceptable excipients.

In another embodiment, there is provided the pharmaceutical composition, further comprising an additional therapeutic agent. In a further embodiment, the additional therapeutic agent is selected from the group consisting of nucleoside reverse transcription inhibitors (NRTIs), non-nucleoside reverse transcriptase inhibitors (NNRTIs), protease inhibitors (PIs), integrase inhibitors, CCR5 inhibitors, fusion inhibitors and maturation inhibitors (MIs) and any combination thereof. These active ingredients are formulated for simultaneous, separate or sequential administration. When the active ingredients are administered sequentially, either ((((((R)-1-(6-amino-9H-purin-9-yl)propan-2-yl)oxy)methyl)(phenoxy)phosphoryl)oxy) methyl pivalate or additional therapeutic agent, may be administered first. When administration is simultaneous, the active ingredients may be administered either in the same or different pharmaceutical compositions. Adjunctive therapy, i.e. where one active ingredient is used as the primary treatment and the other active ingredient(s) is/are used to assist that primary treatment is also an embodiment of the present invention.

In yet another embodiment, the pharmaceutical composition is a combination of ((((((R)-1-(6-amino-9H-purin-9-yl)propan-2-yl)oxy)methyl)(phenoxy)phosphoryl)oxy) methyl pivalate or a pharmaceutically acceptable derivative thereof and one or more of additional therapeutic agent selected from, but not limiting to, emtricitabine, efavirenz, nevirapine, darunavir, atazanavir, zidovudine, didanosine, stavudine, lamivudine, zalcitabine, abacavir sulphate, delavirdine, saquinavir, indinavir, ritonavir, nelfinavir, amprenavir, cobicistat, lopinavir, enfuvirtide, dolutegravir, elvitegravir, raltegravir, rilpivirine.

In yet another embodiment, the pharmaceutical composition is a combination of ((((((R)-1-(6-amino-9H-purin-9-yl)propan-2-yl)oxy)methyl)(phenoxy)phosphoryl)oxy) methyl pivalate or a pharmaceutically acceptable derivative thereof and emtricitabine.

In yet another embodiment, the pharmaceutical composition is a combination of ((((((R)-1-(6-amino-9H-purin-9-yl)propan-2-yl)oxy)methyl)(phenoxy)phosphoryl)oxy) methyl pivalate or a pharmaceutically acceptable derivative thereof, and lamivudine.

In yet another embodiment, the pharmaceutical composition is a combination of ((((((R)-1-(6-amino-9H-purin-9-yl)propan-2-yl)oxy)methyl)(phenoxy)phosphoryl)oxy) methyl pivalate or a pharmaceutically acceptable derivative thereof, lamivudine and efavirenz.

In yet another embodiment, the pharmaceutical composition is a combination of ((((((R)-1-(6-amino-9H-purin-9-yl)propan-2-yl) oxy)methyl)(phenoxy)phosphoryl)oxy) methyl pivalate or a pharmaceutically acceptable derivative thereof, emtricitabine and efavirenz.

In yet another embodiment, the pharmaceutical composition is a combination of ((((((R)-1-(6-amino-9H-purin-9-yl)propan-2-yl)oxy)methyl)(phenoxy)phosphoryl)oxy) methyl pivalate or a pharmaceutically acceptable derivative thereof, emtricitabine, and rilpivirine.

In yet another embodiment, the pharmaceutical composition is a combination of ((((((R)-1-(6-amino-9H-purin-9-yl)propan-2-yl)oxy)methyl)(phenoxy)phosphoryl)oxy) methyl pivalate or a pharmaceutically acceptable derivative thereof, elvitegravir, cobicistat, and emtricitabine.

In yet another embodiment, the pharmaceutical composition is a combination of ((((((R)-1-(6-amino-9H-purin-9-yl)propan-2-yl)oxy)methyl)(phenoxy)phosphoryl)oxy) methyl pivalate or a pharmaceutically acceptable derivative thereof and entecavir.

In yet another embodiment, the pharmaceutical composition is a combination of ((((((R)-1-(6-amino-9H-purin-9-yl)propan-2-yl)oxy)methyl)(phenoxy)phosphoryl)oxy) methyl pivalate or a pharmaceutically acceptable derivative thereof and one or more of additional therapeutic agent selected from, but not limiting to, recombinant Human Interferon Alfa such as pegylated interferon alfa-2a or pegylated interferon alfa-2b (collectively "peginterferon" or "PEG"), nucleoside analogs for example ribavirin, direct acting antivirals (for example daclatasvir, boceprevir and telapravir), NS3/4A protease inhibitors (PIs) (for example simeprevir), nucleotide NS5B polymerase inhibitors (for example sofosbuvir), NS5A Inhibitors (for example daclatasvir), non-nucleoside NS5B Polymerase Inhibitors (for example dasabuvir).

In yet another embodiment, the pharmaceutical composition is a combination of ((((((R)-1-(6-amino-9H-purin-9-yl)propan-2-yl)oxy)methyl)(phenoxy)phosphoryl)oxy) methyl pivalate or a pharmaceutically acceptable derivative thereof and one or more of additional therapeutic agent selected from, but not limiting to, peginterferon, ribavirin, sofosbuvir, daclatasvir, velpatasvir, voxilaprevir, boceprevir, telaprevir, simeprevir, dasabuvir, ledipasvir, ombitasvir, paritaprevir, ritonavir, elbasvir, grazoprevir, asunaprevir, beclabuvir.

The term "combination" as used herein, defines either a fixed combination in one dosage unit form, a non-fixed combination or a kit containing individual parts for combined administration.

((((((R)-1-(6-amino-9H-purin-9-yl)propan-2-yl)oxy) methyl)(phenoxy)phosphoryl)oxy) methyl pivalate is useful in the treatment and/or prophylaxis of one or more viral infections in man or animals, including infections caused by DNA viruses. RNA viruses, herpesviruses (e.g., CMV, HSV 1, HSV 2, VZV), retroviruses, hepadnaviruses (e.g., HBV), papillomavirus, hantavirus, adenoviruses and HIV. U.S. Pat. No. 6,043,230 (incorporated by reference herein in its entirety) and other publications describe the antiviral specificity of nucleotide analogs, such as tenofovir disoproxil. Like tenofovir disoproxil, ((((((R)-1-(6-amino-9H-purin-9-yl)propan-2-yl)oxy)methyl)(phenoxy)phosphoryl)oxy) methyl pivalate is another prodrug form of tenofovir, and can be used in the treatment and/or prophylaxis of the same conditions.

In one embodiment, there is provided a method for treating a human immunodeficiency virus (HIV) infection comprising administering to a subject in need thereof a therapeutically effective amount of comprising ((((((R)-1-(6-amino-9H-purin-9-yl) propan-2-yl)oxy)methyl)(phenoxy)phosphoryl)oxy)methyl pivalate or a pharmaceutically acceptable derivative thereof.

In another embodiment, there is provided a method for treating an HIV infection comprising administering to a subject in need thereof a therapeutically effective amount of a pharmaceutical composition comprising ((((((R)-1-(6-amino-9H-purin-9-yl)propan-2-yl)oxy)methyl)(phenoxy) phosphoryl)oxy)methyl pivalate or a pharmaceutically acceptable derivative thereof. In a further embodiment, the method comprises administering to the subject one or more additional therapeutic agents selected from the group consisting of nucleoside reverse transcription inhibitors (NRTIs), non-nucleoside reverse transcriptase inhibitors (NNRTIs), protease inhibitors (PIs), integrase inhibitors, CCR5 inhibitors, fusion inhibitors and maturation inhibitors (MIs) and any combination thereof.

In yet another embodiment, there is provided a method for treating a hepatitis B virus (HBV) infection comprising administering to a subject in need thereof a therapeutically effective amount of ((((((R)-1-(6-amino-9H-purin-9-yl)propan-2-yl)oxy)methyl)(phenoxy)phosphoryl)oxy)methyl pivalate or a pharmaceutically acceptable derivative thereof.

In another embodiment, there is provided a method for treating an HBV infection comprising administering to a subject in need thereof a therapeutically effective amount of the pharmaceutical composition comprising ((((((R)-1-(6-amino-9H-purin-9-yl)propan-2-yl)oxy)methyl)(phenoxy) phosphoryl)oxy)methyl pivalate or a pharmaceutically acceptable derivative thereof.

In yet another embodiment, there is provided a method for treating a hepatitis C virus (HCV) infection comprising administering to a subject in need thereof a therapeutically effective amount of ((((((R)-1-(6-amino-9H-purin-9-yl)propan-2-yl)oxy)methyl)(phenoxy)phosphoryl)oxy)methyl pivalate or a pharmaceutically acceptable derivative thereof.

In another embodiment, there is provided a method for treating an HCV infection comprising administering to a subject in need thereof a therapeutically effective amount of the pharmaceutical composition comprising ((((((R)-1-(6-amino-9H-purin-9-yl)propan-2-yl)oxy)methyl)(phenoxy) phosphoryl)oxy)methyl pivalate or a pharmaceutically acceptable derivative thereof.

In one embodiment, there is provided a method for preparing a pharmaceutical composition comprising combining ((((((R)-1-(6-amino-9H-purin-9-yl)propan-2-yl)oxy) methyl)(phenoxy)phosphoryl)oxy)methyl pivalate or a pharmaceutically acceptable derivative thereof and a pharmaceutically acceptable excipient to provide the pharmaceutical composition.

In one embodiment, there is provided the use of ((((((R)-1-(6-amino-9H-purin-9-yl) propan-2-yl)oxy)methyl)(phenoxy)phosphoryl)oxy)methyl pivalate or a pharmaceutically acceptable derivative thereof for the prophylactic or therapeutic treatment of an HIV infection. In a further embodiment, there is provided the use of ((((((R)-1-(6-amino-9H-purin-9-yl) propan-2-yl)oxy)methyl)(phenoxy)phosphoryl) oxy)methyl pivalate or a pharmaceutically acceptable derivative thereof for the preparation or manufacture of a medicament for the treatment of an HIV infection.

In one embodiment, there is provided the use of ((((((R)-1-(6-amino-9H-purin-9-yl) propan-2-yl)oxy)methyl)(phenoxy)phosphoryl)oxy)methyl pivalate or a pharmaceutically acceptable derivative thereof for the prophylactic or therapeutic treatment of an HBV infection. In a further embodiment is provided the use of ((((((R)-1-(6-amino-9H-purin-9-yl) propan-2-yl)oxy)methyl)(phenoxy)phosphoryl)oxy) methyl pivalate or a pharmaceutically acceptable derivative thereof for the preparation or manufacture of a medicament for the treatment of an HBV infection.

In one embodiment, there is provided the use of ((((((R)-1-(6-amino-9H-purin-9-yl) propan-2-yl)oxy)methyl)(phenoxy)phosphoryl)oxy)methyl pivalate or a pharmaceutically acceptable derivative thereof for the prophylactic or therapeutic treatment of an HCV infection. In a further embodiment is provided the use of ((((((R)-1-(6-amino-9H-purin-9-yl) propan-2-yl)oxy)methyl)(phenoxy)phosphoryl)oxy) methyl pivalate or a pharmaceutically acceptable derivative thereof for the preparation or manufacture of a medicament for the treatment of an HCV infection.

In some embodiments of the invention, the methods of prophylactic or therapeutic treatment comprise administration of multiple daily doses. In other embodiments, the methods of prophylactic or therapeutic treatment comprise administration of a single daily dose.

((((((R)-1-(6-amino-9H-purin-9-yl)propan-2-yl)oxy) methyl)(phenoxy)phosphoryl)oxy) methyl pivalate can be administered by any route appropriate to the condition to be treated. Suitable routes include oral, rectal, nasal, topical (including ocular, buccal, and sublingual), vaginal, and parenteral (including subcutaneous, intramuscular, intravenous, intradermal, intrathecal, and epidural). Generally, ((((((R)-1-(6-amino-9H-purin-9-yl)propan-2-yl)oxy) methyl)(phenoxy)phosphoryl)oxy)methyl pivalate is administered orally, but it can be administered by any of the other routes noted herein. The formulations are in unit dosage form and are prepared by any of the methods well known in the art of pharmacy.

For oral therapeutic administration, ((((((R)-1-(6-amino-9H-purin-9-yl)propan-2-yl)oxy)methyl)(phenoxy)phosphoryl)oxy)methyl pivalate may be combined with one or more excipients and used in the form of ingestible tablets, dispersible tablets, buccal tablets, troches, capsules, elixirs, solutions, suspensions, syrups, wafers, Self-emulsifying drug delivery system (SEDDS), Self-microemulsifying drug delivery system (SMEDDS) and the like. Such pharmaceutical compositions and preparations will typically contain at least 0.1% of ((((((R)-1-(6-amino-9H-purin-9-yl)propan-2-yl)oxy)methyl)(phenoxy)phosphoryl)oxy)methyl pivalate. The percentage of this active compound in the compositions and preparations may, of course, be varied and may conveniently be between about 2% to about 80%, preferably between about 3% to about 50%, more preferably between about 5% to about 25% of the weight of a given unit dosage form. The amount of active compound in such therapeutically useful pharmaceutical compositions is preferably such that an effective dosage level will be obtained upon administration of a single-unit dosage (e.g., tablet). Other dosage formulations may provide therapeutically effective amounts of ((((((R)-1-(6-amino-9H-purin-9-yl)propan-2-yl)oxy)

methyl)(phenoxy)phosphoryl)oxy)methyl pivalate upon repeated administration of subclinically effective amounts of the same. Preferred unit dosage formulations include those containing a daily dose (e.g., a single daily dose), as well as those containing a unit daily subclinical dose, or an appropriate fraction thereof (e.g., multiple daily doses), of ((((((R)-1-(6-amino-9H-purin-9-yl)propan-2-yl)oxy) methyl)(phenoxy)phosphoryl)oxy)methyl pivalate.

Pharmaceutical compositions suitable for oral administration may be presented as discrete units such as capsules, cachets, or tablets, each containing a predetermined amount of ((((((R)-1-(6-amino-9H-purin-9-yl)propan-2-yl)oxy) methyl)(phenoxy)phosphoryl)oxy)methyl pivalate; as a powder or granules; as a solution or a suspension in an aqueous liquid or a nonaqueous liquid; or as an oil-in-water liquid emulsion or a water-in-oil liquid emulsion. ((((((R)-1-(6-amino-9H-purin-9-yl)propan-2-yl)oxy)methyl)(phenoxy)phosphoryl)oxy)methyl pivalate may also be presented as a bolus, electuary, or paste.

((((((R)-1-(6-amino-9H-purin-9-yl)propan-2-yl)oxy) methyl)(phenoxy)phosphoryl)oxy) methyl pivalate is preferably administered as part of a pharmaceutical composition or formulation. Such pharmaceutical composition or formulation comprises ((((((R)-1-(6-amino-9H-purin-9-yl)propan-2-yl)oxy)methyl)(phenoxy)phosphoryl)oxy)methyl pivalate together with one or more pharmaceutically acceptable carriers/excipients, and optionally other therapeutic ingredients. The excipient(s)/carrier(s) must be "acceptable" in the sense of being compatible with the other ingredients of the formulation and not deleterious to the patient. Excipients include, but are not limited to, substances that can serve as a vehicle or medium for ((((((R)-1-(6-amino-9H-purin-9-yl) propan-2-yl)oxy)methyl)(phenoxy)phosphoryl)oxy) methyl pivalate (e.g., a diluent carrier). They may be enclosed in hard or soft shell gelatin capsules, may be compressed into tablets, or may be incorporated directly with the food of the patient's diet.

Suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

In one embodiment, the pharmaceutical composition may contain 1-80% diluent, 1-50% binder, 10-20% disintegrant, 1-10% lubricant, 0.5-5% glidant, and 1-10% coating agents.

Accordingly, the tablets, troches, pills, capsules, and the like may also contain, without limitation, the following: a binder(s), such as hydroxypropyl cellulose, povidone, or hydroxypropyl methylcellulose; a filler(s), such as microcrystalline cellulose, pregelatinized starch, starch, mannitol, or lactose monohydrate; a disintegrating agent(s), such as croscarmellose sodium, cross-linked povidone, or sodium starch glycolate; a lubricant(s), such as magnesium stearate, stearic acid, or other metallic stearates; a sweetening agent(s), such as sucrose, fructose, lactose, or aspartame; and/or a flavoring agent(s), such as peppermint, oil of wintergreen, or a cherry flavoring. When the unit dosage form is a capsule, it may contain, in addition to materials of the above types, a liquid carrier, such as a vegetable oil or a polyethylene glycol. Various other materials may be present as coatings or to otherwise modify the physical form of the solid unit dosage form. For instance, tablets, pills, or capsules may be coated with gelatin, polymers, wax, shellac, or sugar and the like. In addition, ((((((R)-1-(6-amino-9H-purin-9-yl)propan-2-yl)oxy)methyl)(phenoxy)phosphoryfloxy)methyl pivalate may be incorporated into sustained-release preparations and devices.

For infections of the eye or other external tissues, e.g., mouth and skin, the pharmaceutical compositions are preferably applied as a topical ointment or cream or gel containing ((((((R)-1-(6-amino-9H-purin-9-yl)propan-2-yl)oxy) methyl)(phenoxy)phosphoryfloxy)methyl pivalate in an amount of, for example, 0.01 to 10% w/w, preferably 0.2 to 5% w/w and most preferably 0.5 to 2% w/w. When formulated in an ointment, the active ingredient may be employed with either a paraffinic or a water-miscible ointment base. Alternatively, the active ingredient may be formulated in a cream with an oil-in-water cream base.

Pharmaceutical compositions suitable for topical administration in the mouth include lozenges comprising ((((((R)-1-(6-amino-9H-purin-9-yl)propan-2-yl)oxy)methyl)(phenoxy)phosphoryl)oxy)methyl pivalate in a flavored basis, for example, sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations for vaginal administration may be presented as a vaginal ring, implant, gel, cream spray foam, or suppository.

Pharmaceutical formulations suitable for parenteral administration are sterile and include aqueous and nonaqueous injection solutions that may contain antioxidants, buffers, bacteriostats, and solutes that render the formulation isotonic with the blood of the intended recipient; and aqueous and nonaqueous sterile suspensions that may include suspending agents and thickening agents. The formulations may be presented in unit-dose or multi-dose containers, for example, sealed ampoules and vials with elastomeric stoppers, and may be stored in a freeze-dried (lyophilized) condition requiring only the addition of the sterile liquid carrier (e.g., water for injections) immediately prior to use. Injection solutions and suspensions may be prepared from sterile powders, granules, and tablets of the kind previously described.

In addition to the ingredients particularly mentioned above, the pharmaceutical compositions/formulations may include other ingredients conventional in the art, having regard to the type of formulation in question.

In another embodiment, there is provided veterinary compositions comprising ((((((R)-1-(6-amino-9H-purin-9-yl) propan-2-yl)oxy)methyl)(phenoxy)phosphoryl)oxy)methyl pivalate together with a veterinary carrier therefor. Veterinary carriers are materials useful for the purpose of administering the composition to cats, dogs, horses, rabbits, and other animals, and may be solid, liquid, or gaseous materials that are otherwise inert or acceptable in the veterinary art and are compatible with the active ingredient. These veterinary compositions may be administered orally, parenterally, or by any other desired route.

((((((R)-1-(6-amino-9H-purin-9-yl)propan-2-yl)oxy) methyl)(phenoxy)phosphoryl)oxy) methyl pivalate can be used to provide controlled release pharmaceutical formulations containing a matrix or absorbent material and an active ingredient of the invention, in which the release of the active ingredient can be controlled and regulated to allow less frequent dosing or to improve the pharmacokinetic or toxicity profile of the compound. Controlled release formulations adapted for oral administration, in which discrete units comprising a compounds of the invention, can be prepared according to conventional methods.

In one embodiment, ((((((R)-1-(6-amino-9H-purin-9-yl)propan-2-yl)oxy)methyl)(phenoxy)phosphoryl)oxy)methyl pivalate may be present in the form of nanoparticles which have an average particle size of less than 2,000 nm, less than 1,500 nm, less than 1,000 nm, less than 750 nm, less than 500 nm, or less than 250 nm.

Useful dosages of ((((((R)-1-(6-amino-9H-purin-9-yl)propan-2-yl)oxy)methyl)(phenoxy)phosphoryl)oxy)methyl pivalate can be determined by comparing in vitro activities, and the in vivo activities in animal models. Methods for the extrapolation of effective amounts/dosages in mice and other animals to therapeutically effective amounts/dosages in humans are known in the art.

The amount of ((((((R)-1-(6-amino-9H-purin-9-yl)propan-2-yl)oxy)methyl)(phenoxy)phosphoryl)oxy)methyl pivalate required for use in treatment will vary with several factors, including but not limited to the route of administration, the nature of the condition being treated, and the age and condition of the patient; ultimately, the amount administered will be at the discretion of the attendant physician or clinician. The therapeutically effective amount/dose of ((((((R)-1-(6-amino-9H-purin-9-yl)propan-2-yl)oxy)methyl)(phenoxy)phosphoryl)oxy)methyl pivalate depends, at least, on the nature of the condition being treated, any toxicity or drug interaction issues, whether the compound is being used prophylactically (e.g., sometimes requiring lower doses) or against an active disease or condition, the method of delivery, and the pharmaceutical formulation, and will be determined by the clinician using conventional dose escalation studies.

In one embodiment, the oral dose of ((((((R)-1-(6-amino-9H-purin-9-yl)propan-2-yl)oxy)methyl)(phenoxy)phosphoryl)oxy)methyl pivalate may be in the range from about 0.0001 to about 100 mg/kg body weight per day, for example, from about 0.01 to about 10 mg/kg body weight per day, from about 0.01 to about 5 mg/kg body weight per day, from about 0.5 to about 50 mg/kg body weight per day, from about 1 to about 30 mg/kg body weight per day, from about 1.5 to about 10 mg/kg body weight per day, or from about 0.05 to about 0.5 mg/kg body weight per day. As a nonlimiting example, the daily candidate dose for an adult human of about 70 kg body weight will range from about 0.1 mg to about 500 mg, or from about 1 mg to about 500 mg, or from about 5 mg to about 300 mg, or from about 10 mg to about 150 mg, or from about 25 mg to about 150 mg, or from about 5 mg to about 100 mg, and may take the form of single or multiple doses.

In one embodiment, ((((((R)-1-(6-amino-9H-purin-9-yl)propan-2-yl)oxy)methyl)(phenoxy)phosphoryl)oxy)methyl pivalate or pharmaceutically acceptable derivative thereof exhibits potent anti-HIV activity 500- to 1000-fold enhanced activity relative to tenofovir against HIV-1 in T cells, activated peripheral blood mononuclear lymphocytes (PBMCs), and macrophages.

In certain embodiments, the administration of ((((((R)-1-(6-amino-9H-purin-9-yl) propan-2-yl)oxy)methyl)(phenoxy)phosphoryl)oxy)methyl pivalate or pharmaceutically acceptable derivative thereof, either alone or in combination with one or more additional therapeutic agent, can lower detectable viral RNA/DNA levels in a patient. For instance, methods disclosed herein can lower viral RNA/DNA levels by at least 10%, at least 20%, at least 30%, at least 40%, at least 50%, at least 60%, at least 70%, at least 80%, at least 90%, or at least 95% relative to viral RNA/DNA levels prior to initiating treatment. In some instances, ((((((R)-1-(6-amino-9H-purin-9-yl)propan-2-yl)oxy)methyl)(phenoxy)phosphoryl)oxy)methyl pivalate or pharmaceutically acceptable derivative thereof can be administered to a patient such that no viral RNA/DNA levels is detectable in the patient after the treatment course is complete. Viral RNA/DNA levels can be determined by quantitative, multi-cycle reverse transcriptase PCR. Such techniques are known, for instance in U.S. 6,172,046, col. 4, line 50—col. 6, line 5, which is hereby incorporated by reference. As used herein, no detectable viral RNA/DNA levels describes a condition in which there are less than 100 copies per ml serum of the patient.

Therapeutic methods include administering ((((((R)-1-(6-amino-9H-purin-9-yl) propan-2-yl)oxy)methyl)(phenoxy)phosphoryl)oxy)methyl pivalate to a subject/patient in need of the same as a therapeutic or prophylactic treatment. Thus, ((((((R)-1-(6-amino-9H-purin-9-yl) propan-2-yl)oxy)methyl)(phenoxy)phosphoryl)oxy)methyl pivalate may be administered to a subject/patient having a medical disorder or to a subject who may acquire the disorder. One of ordinary skill will appreciate that such treatment is given in order to ameliorate, prevent, delay, cure, and/or reduce the severity of a symptom or set of symptoms of a disorder (including a recurring disorder). The treatment may also be given to prolong the survival of a subject, e.g., beyond the survival time expected in the absence of such treatment. The medical disorders that may be treated with ((((((R)-1-(6-amino-9H-purin-9-yl)propan-2-yl)oxy)methyl)(phenoxy)phosphoryl)oxy)methyl pivalate include those discussed herein, including without limitation, HIV infection, HBV infection and HCV infection.

In order that this invention be more fully understood, the following examples are set forth. These examples are for the purpose of illustration only and are not to be construed as limiting the scope of the invention in any way. The following compositions are prepared by any of the process/methods well known in the art of pharmacy.

Example 1—((((((R)-1-(6-amino-9H-purin-9-yl)propan-2-yl)oxy)methyl)(phenoxy) phosphoryl)oxy)methyl pivalate fumarate tablets

| Ingredient | Qty (% w/w) |
|---|---|
| Dry mix | |
| ((((((R)-1-(6-amino-9H-purin-9-yl)propan-2-yl)oxy)methyl)(phenoxy)phosphoryl) oxy)methyl pivalate fumarate | 2%-80% |
| Microcrystalline Cellulose | 10%-40% |
| Lactose | 10%-70% |
| Croscarmellose sodium | 2%-10% |
| Blending & Lubrication | |
| Colloidal silicon dioxide | 1%-10% |
| Magnesium Stearate | 0.5%-5% |
| Film Coating | |
| Opadry | 1%-10% |

Example 2—((((((R)-1-(6-amino-9H-purin-9-yl)propan-2-yl)oxy)methyl)(phenoxy) phosphoryl)oxy)methyl pivalate fumarate tablets

| Ingredient | Qty (% w/w) |
|---|---|
| Dry mix | |
| ((((((R)-1-(6-amino-9H-purin-9-yl)propan-2-yl)oxy)methyl)(phenoxy)phosphoryl) oxy)methyl pivalate fumarate | 15.08 |
| Microcrystalline Cellulose | 16.99 |
| Anhydrous lactose | 60.64 |
| Croscarmellose sodium | 3.39 |
| Blending & Lubrication | |
| Colloidal silicon dioxide | |
| Magnesium Stearate | 0.97 |
| Film Coating | |
| Opadry | 3 |

Example 3—((((((R)-1-(6-amino-9H-purin-9-yl)propan-2-yl)oxy)methyl)(phenoxy) phosphoryl)oxy)methyl pivalate fumarate tablets

| Ingredient | Qty (% w/w) |
|---|---|
| Dry mix | |
| ((((((R)-1-(6-amino-9H-purin-9-yl)propan-2-yl)oxy)methyl)(phenoxy)phosphoryl) oxy)methyl pivalate fumarate | 50 |
| Microcrystalline Cellulose | 16.5 |
| Anhydrous lactose | 25 |
| Croscarmellose sodium | 4 |
| Blending & Lubrication | |
| Colloidal silicon dioxide | 0.5 |
| Magnesium Stearate | 1 |
| Film Coating | |
| Opadry | 3 |

Example 4—((((((R)-1-(6-amino-9H-purin-9-yl)propan-2-yl)oxy)methyl)(phenoxy) phosphoryl)oxy)methyl pivalate fumarate dispersible tablets

| Ingredient | Qty (% w/w) |
|---|---|
| Dry mix | |
| ((((((R)-1-(6-amino-9H-purin-9-yl)propan-2-yl)oxy)methyl)(phenoxy)phosphoryl) oxy)methyl pivalate fumarate | 15.54 |
| Mannitol | 76.88 |
| Croscarmellose sodium | 5.00 |
| Sodium saccharin | 1.00 |
| Strawberry flavor | 0.50 |
| Iron oxide Red | 0.075 |
| Blending and Lubrication | |
| Magnesium Stearate | 1.00 |

Example 5—((((((R)-1-(6-amino-9H-purin-9-yl)propan-2-yl)oxy)methyl)(phenoxy) phosphoryl)oxy)methyl pivalate fumarate oral powder for suspension

| Ingredient | Qty (% w/w) |
|---|---|
| Dry mix | |
| ((((((R)-1-(6-amino-9H-purin-9-yl)propan-2-yl)oxy)methyl)(phenoxy)phosphoryl) oxy)methyl pivalate fumarate | 15.54 |
| Sorbitol Powder | 74.71 |
| Xanthum gum | 1.5 |
| Monosodium citrate (anhydrous) | 5.50 |
| Sodium Benzoate | 0.25 |
| Cream caramel flavour | 1.00 |
| Saccharin sodium | 1.00 |
| Titanium dioxide | 0.50 |

Example 6—((((((R)-1-(6-amino-9H-purin-9-yl)propan-2-yl)oxy)methyl)(phenoxy) phosphoryl)oxy)methyl pivalate fumarate oral granules

| Ingredient | Qty (% w/w) |
|---|---|
| Dry mix | |
| ((((((R)-1-(6-amino-9H-purin-9-yl)propan-2-yl)oxy)methyl)(phenoxy)phosphoryl) oxy)methyl pivalate fumarate | 15.54 |
| Mannitol NF (Pearlitol 200 SD) | 76.88 |
| Hydroxypropyl cellulose NF (Klucel MF) | 5.00 |
| Ethyl cellulose NF (Ethocel E7) | 2.075 |
| Silicon dioxide NF | 0.50 |

Example 7—Emtricitabine+((((((R)-1-(6-amino-9H-purin-9-yl)propan-2-yl)oxy)methyl)(phenoxy)phosphoryl)oxy)methyl pivalate fumarate tablets

| Ingredients | Qty (% w/w) |
|---|---|
| Emtricitabine | 48.54 |
| ((((((R)-1-(6-amino-9H-purin-9-yl)propan-2-yl)oxy)methyl)(phenoxy)phosphoryl) oxy)methyl pivalate fumarate | 6.07 |
| MCC (Avicel Ph 101) | 37.14 |
| Croscarmellose sodium (Ac-di-sol) | 2.43 |
| Magnesium stearate | 0.24 |
| Blending and lubrication | |
| Croscarmellose sodium | 2.43 |
| Magnesium stearate | 0.24 |
| Coating | |
| Opadry Yellow | 2.91 |
| Purified water | qs |

Example 8—Efavirenz+((((((R)-1-(6-amino-9H-purin-9-yl)propan-2-yl)oxy) methyl)(phenoxy)phosphoryl) oxy)methyl pivalate fumarate tablets

| Ingredients | Qty (% w/w) |
|---|---|
| Efavirenz | 48.54 |
| ((((((R)-1-(6-amino-9H-purin-9-yl)propan-2-yl)oxy)methyl)(phenoxy)phosphoryl) oxy)methyl pivalate fumarate | 2.02 |
| MCC (Avicel Ph 101) | 44.74 |
| Croscarmellose sodium (Ac-di-sol) | 0.81 |
| Magnesium stearate | 0.08 |
| Blending and lubrication | |
| Croscarmellose sodium | 0.81 |
| Magnesium stearate | 0.08 |
| Coating | |
| Opadry Yellow | 2.91 |
| Purified water | qs |

Example 9—Nevirapine+((((((R)-1-(6-amino-9H-purin-9-yl)propan-2-yl)oxy) methyl)(phenoxy)phosphoryl) oxy)methyl pivalate fumarate tablets

| Ingredients | Qty (% w/w) |
|---|---|
| Nevirapine | 48.54 |
| ((((((R)-1-(6-amino-9H-purin-9-yl)propan-2-yl)oxy)methyl)(phenoxy)phosphoryl) oxy)methyl pivalate fumarate | 3.03 |
| MCC (Avicel Ph 101) | 42.84 |
| Croscarmellose sodium (Ac-di-sol) | 1.21 |
| Magnesium stearate | 0.12 |
| Blending and lubrication | |
| Croscarmellose sodium | 1.21 |
| Magnesium stearate | 0.12 |
| Coating | |
| Opadry Yellow | 2.91 |
| Purified water | qs |

Example 10—Elvitegravir+((((((R)-1-(6-amino-9H-purin-9-yl)propan-2-yl)oxy) methyl)(phenoxy)phosphoryl) oxy)methyl pivalate fumarate tablets

| Ingredients | Qty (% w/w) |
|---|---|
| Elvitegravir | 48.54 |
| ((((((R)-1-(6-amino-9H-purin-9-yl)propan-2-yl)oxy)methyl)(phenoxy)phosphoryl) oxy)methyl pivalate fumarate | 8.09 |
| MCC (Avicel Ph 101) | 33.33 |
| Croscarmellose sodium (Ac-di-sol) | 3.24 |
| Magnesium stearate | 0.32 |
| Blending and lubrication | |
| Croscarmellose sodium | 3.24 |
| Magnesium stearate | 0.32 |
| Coating | |
| Opadry Yellow | 2.91 |
| Purified water | qs |

Example 11—Raltegravir+((((((R)-1-(6-amino-9H-purin-9-yl)propan-2-yl)oxy) methyl)(phenoxy)phosphoryl) oxy)methyl pivalate fumarate tablets

| Ingredients | Qty (% w/w) |
|---|---|
| Raltegravir | 48.54 |
| ((((((R)-1-(6-amino-9H-purin-9-yl)propan-2-yl)oxy)methyl)(phenoxy)phosphoryl) oxy)methyl pivalate fumarate | 3.03 |
| MCC (Avicel Ph 101) | 42.84 |
| Croscarmellose sodium (Ac-di-sol) | 1.21 |
| Magnesium stearate | 0.12 |
| Blending and lubrication | |
| Croscarmellose sodium | 1.21 |
| Magnesium stearate | 0.12 |
| Coating | |
| Opadry Yellow | 2.91 |
| Purified water | qs |

Example 12—Dolutegravir+((((((R)-1-(6-amino-9H-purin-9-yl)propan-2-yl)oxy) methyl)(phenoxy)phosphoryl) oxy)methyl pivalate fumarate tablets

| Ingredients | Qty (% w/w) |
|---|---|
| Dolutegravir | 24.27 |
| ((((((R)-1-(6-amino-9H-purin-9-yl)propan-2-yl)oxy)methyl)(phenoxy)phosphoryl) oxy)methyl pivalate fumarate | 12.14 |
| MCC (Avicel Ph 101) | 50.00 |
| Croscarmellose sodium (Ac-di-sol) | 4.85 |
| Magnesium stearate | 0.49 |
| Blending and lubrication | |
| Croscarmellose sodium | 4.85 |
| Magnesium stearate | 0.49 |
| Coating | |
| Opadry Yellow | 2.91 |
| Purified water | qs |

Example 13—Atazanavir+((((((R)-1-(6-amino-9H-purin-9-yl)propan-2-yl)oxy) methyl)(phenoxy)phosphoryl) oxy)methyl pivalate fumarate tablets

| Ingredients | Qty (% w/w) |
|---|---|
| Atazanavir | 48.54 |
| ((((((R)-1-(6-amino-9H-purin-9-yl)propan-2-yl)oxy)methyl)(phenoxy)phosphoryl) oxy)methyl pivalate fumarate | 4.05 |
| MCC (Avicel Ph 101) | 40.94 |
| Croscarmellose sodium (Ac-di-sol) | 1.62 |
| Magnesium stearate | 0.16 |
| Blending and lubrication | |
| Croscarmellose sodium | 1.62 |
| Magnesium stearate | 0.16 |
| Coating | |
| Opadry Yellow | 2.91 |
| Purified water | qs |

Example 14—Darunavir+((((((R)-1-(6-amino-9H-purin-9-yl)propan-2-yl)oxy) methyl)(phenoxy)phosphoryl) oxy)methyl pivalate fumarate tablets

| Ingredients | Qty (% w/w) |
| --- | --- |
| Darunavir | 36.41 |
| ((((((R)-1-(6-amino-9H-purin-9-yl)propan-2-yl)oxy)methyl)(phenoxy)phosphoryl) oxy)methyl pivalate fumarate | 12.14 |
| MCC (Avicel Ph 101) | 37.86 |
| Croscarmellose sodium (Ac-di-sol) | 4.85 |
| Magnesium stearate | 0.49 |
| Blending and lubrication | |
| Croscarmellose sodium | 4.85 |
| Magnesium stearate | 0.49 |
| Coating | |
| Opadry Yellow | 2.91 |
| Purified water | qs |

Example 15—Cobicistat+((((((R)-1-(6-amino-9H-purin-9-yl)propan-2-yl)oxy) methyl)(phenoxy)phosphoryl) oxy)methyl pivalate fumarate tablets

| Ingredients | Qty (% w/w) |
| --- | --- |
| Cobicistat | 48.54 |
| ((((((R)-1-(6-amino-9H-purin-9-yl)propan-2-yl)oxy)methyl)(phenoxy)phosphoryl) oxy)methyl pivalate fumarate | 8.09 |
| MCC (Avicel Ph 101) | 33.33 |
| Croscarmellose sodium (Ac-di-sol) | 3.24 |
| Magnesium stearate | 0.32 |
| Blending and lubrication | |
| Croscarmellose sodium | 3.24 |
| Magnesium stearate | 0.32 |
| Coating | |
| Opadry Yellow | 2.91 |
| Purified water | qs |

Example 16: Vaginal Ring

| Ingredients | Qty (% w/w) |
| --- | --- |
| ((((((R)-1-(6-amino-9H-purin-9-yl)propan-2-yl)oxy)methyl)(phenoxy)phosphoryl) oxy)methyl pivalate fumarate | 1.00 |
| Hydroxyethylcellulose | 2.50 |
| Propylparaben | 0.02 |
| Methylparaben | 0.18 |
| Edetate Disodium | 0.05 |
| Glycerin | 20.00 |
| Citric Acid | 1.00 |
| Purified Water | 75.25 |

In order that this invention be more fully understood, the following preparative and testing methods are set forth. These methods are for the purpose of illustration only and are not to be construed as limiting the scope of the invention in any way.

1. In Vitro Efficacy of ((((((R)-1-(6-amino-9H-purin-9-yl)propan-2-yl) oxy)methyl)(phenoxy)phosphoryl) oxy)methyl Pivalate Fumarate Against HIV-1 in Fresh PBMCs Fresh human PBMCs, seronegative for HIV and HBV, were isolated from screened donors (Biological Specialty Corporation, Colmar, PA). Cells were pelleted/washed 2-3 times by low speed centrifugation and re-suspension in PBS to remove contaminating platelets. The Leukophoresed blood was then diluted 1:1 with Dulbecco's Phosphate Buffered Saline (DPBS) and layered over 15 mL of Ficoll (GE Healthcare #17-1440-02) in 50 mL centrifuge tube and then centrifuged for 30 minutes at 600×g. Banded PBMCs were gently aspirated from the resulting interface and subsequently washed 2× with PBS by low speed centrifugation. After the final wash, cells were enumerated by tryptan blue exclusion and re-suspended at $1 \times 10^6$ cells/mL in RPMI 1640 supplemented with 15% Fetal Bovine Serum (FBS), and 2 mM L-glutamine, 4 μg/mL Phytohemagglutinin (PHA, Sigma). The cells were allowed to incubate for 48-72 hours at 37° C. After incubation, PBMCs were centrifuged and re-suspended in RPMI 1640 with 15% FBS, 2 mM L-glutamine, 100 U/mL penicillin, 100 μg/mL streptomycin, and approximately 100-150 U/mL recombinant human IL-2 (R&D Systems, Inc). IL-2 was included in the culture medium to maintain the cell division initiated by the PHA mitogenic stimulation. PBMCs were maintained in this medium at a concentration of $1\text{-}2 \times 10^6$ cells/mL with biweekly medium changes until used in the assay protocol. Cells were kept in culture for a maximum of two weeks before being deemed too old for use in assays and discarded. MDMs were depleted from the culture as the result of adherence to the tissue culture flask. For the standard PBMC assay, PHA stimulated cells from at least two normal donors were pooled (mixed together), diluted in fresh medium to a final concentration of $1 \times 10^6$ cells/mL, and plated in the interior wells of a 96 well round bottom microplate at 50 μL/well ($5 \times 10^4$ cells/well) in a standard format. Pooling (mixing) of mononuclear cells from more than one donor was used to minimize the variability observed between individual donors, which results from quantitative and qualitative differences in HIV infection and overall response to the PHA and IL-2 of primary lymphocyte populations. Each plate contained virus/cell control wells (cells plus virus), experimental wells (drug plus cells plus virus) and compound control wells (drug plus media without cells, necessary for MTS monitoring of cytotoxicity). In this in vitro assay, PBMC viability remained high throughout the duration of the incubation period. Therefore, infected wells were used in the assessment of both antiviral activity and cytotoxicity. Test drug dilutions were prepared at a 2× concentration in microtiter tubes and 100 μL of each concentration (nine total concentrations) were placed in appropriate wells using the standard format. 50 μL of a predetermined dilution of virus stock was placed in each test well (final MOI approximately 0.1). The PBMC cultures were maintained for six-seven days following infection at 37° C., 5% $CO_2$. After this period, cell-free supernatant samples were collected for analysis of reverse transcriptase activity and/or p24 antigen content.

Following removal of supernatant samples, compound cytotoxicity was measured by addition of MTS to the plates for determination of cell viability. Wells were also examined microscopically and any abnormalities were noted.

A microtiter plate-based reverse transcriptase (RT) reaction was utilized (Buckheit et al., AIDS Research and Human Retroviruses 7:295-302, 1991). Tritiated thymidine triphosphate ($^3$H-TTP, 80 Ci/mmol, NEN) was received in 1:1 dH$_2$O:Ethanol at 1 mCi/mL. Poly rA:oligo dT template: primer (GE Healthcare) was prepared as a stock solution by combining 150 µL poly rA (20 mg/mL) with 0.5 mL oligo dT (20 units/mL) and 5.35 mL sterile dH$_2$O followed by aliquoting (1.0 mL) and storage at −20° C. The RT reaction buffer was prepared fresh on a daily basis and consisted of 125 µL 1.0 M EGTA, 125 µL dH$_2$O, 125 µL 20% Triton X100, 50 µL 1.0 M Tris (pH 7.4), 50 µL 1.0 M DTT, and 40 µL 1.0 M MgCl$_2$. The final reaction mixture was prepared by combining 1 part $^3$H-TTP, 4 parts dH$_2$O, 2.5 parts poly rA:oligo dT stock and 2.5 parts reaction buffer. Ten microliters of this reaction mixture was placed in a round bottom microtiter plate and 15 µL of virus containing supernatant was added and mixed. The plate was incubated at 37° C. for 60 minutes. Following incubation, the reaction volume was spotted onto DE81 filter-mats (Wallac), washed 5 times for 5 minutes each in a 5% sodium phosphate buffer or 2×SSC (Life Technologies). Next they were washed 2 times for 1 minute each in distilled water, 2 times for 1 minute each in 70% ethanol, and then dried. Incorporated radioactivity (counts per minute, CPM) was quantified using standard liquid scintillation techniques.

At assay termination, assay plates were stained with the soluble tetrazolium-based dye MTS (CellTiter 96 Reagent, Promega) to determine cell viability and quantify compound toxicity. The mitochondrial enzymes of metabolically active cells metabolize MTS to yield a soluble formazan product. This allows the rapid quantitative analysis of cell viability and compound cytotoxicity. The MTS was a stable solution that does not require preparation before use. At termination of the assay, 20 µL of MTS reagent was added per well. The microtiter plates were then incubated 4-6 hrs at 37° C. The incubation intervals were chosen based on empirically determined times for optimal dye reduction. Adhesive plate sealers were used in place of the lids, the sealed plate was inverted several times to mix the soluble formazan product and the plate was read spectrophotometrically at 490/650 nm with a Molecular Devices SpectraMaxPlus i3 reader.

Conclusion: The test article was found to be potently active against the two HIV-1 isolates with a high selectivity index indicating high antiviral activity and low toxicity.

| Test article | HIV-1 isolate | EC$_{50}$ (nM) | CC$_{50}$ (nM) | Selectivity Index |
|---|---|---|---|---|
| ((((((R)-1-(6-amino-9H-purin-9-yl)propan-2-yl)oxy)methyl)(phenoxy)phosphoryl) oxy)methyl pivalate fumarate | JV-1083 | 2.46 | 27696 | 11241 |
| ((((((R)-1-(6-amino-9H-purin-9-yl)propan-2-yl)oxy)methyl)(phenoxy)phosphoryl) oxy)methyl pivalate fumarate | 89BZ_167 | 20.8 | 27696 | 1333 |

2. In Vitro Efficacy of ((((((R)-1-(6-amino-9H-purin-9-yl)propan-2-yl) oxy)methyl)(phenoxy)phosphoryl) oxy)methyl Pivalate Fumarate Against HBV Cells in HepG2 Cells The primary anti-HBV assay was performed by using real-time qPCR (TaqMan) to measure extracellular HBV DNA copy number associated with virions released from HepG2 2.2.15 cells. The HepG2 2.2.15 cell line was a stable human hepatoblastoma cell line that contains two copies of the HBV wild-type strain ayw1 genome and constitutively produces high levels of HBV. Antiviral compounds blocking any late step of viral replication such as transcription, translation, pregenome encapsidation, reverse transcription, particle assembly and release can be identified and characterized using this cell line. Briefly, HepG2 2.2.15 cells were plated in 96-well microtiter plates at 1.5×10$^4$ cells/well in Dulbecco's Modified Eagle's Medium supplemented with 2% FBS, 380 µg/mL G418, 2.0 mM L-Glutamine, 100 units/mL Penicillin, 100 µg/mL Streptomycin, and 0.1 mM non-essential amino acids. Only the interior wells were utilized to reduce "edge effects" observed during cell culture; the exterior wells were filled with complete medium to help minimize sample evaporation. After 16-24 hours the confluent monolayer of HepG2 2.2.15 cells was washed and the medium was replaced with complete medium containing various concentrations of a test compound in triplicate. Lamivudine (3TC) was used as the positive control, while media alone was added to cells as a negative control (virus control, VC). Three days later the culture medium was replaced with fresh medium containing the appropriately diluted test compounds. Six days following the initial administration of the test compound, the cell culture supernatant was collected, treated with pronase and then used in a real-time quantitative TaqMan qPCR assay. The PCR-amplified HBV DNA was detected in real-time by monitoring increases in fluorescent signal that result from the exonucleolytic degradation of a quenched fluorescent probe molecule that hybridizes to the amplified HBV DNA. For each PCR amplification, a standard curve was simultaneously generated using dilutions of purified HBV DNA. Antiviral activity was calculated from the reduction in HBV DNA levels (EC$_{50}$ values determined). A tetrazolium dye (MTS; 3-(4,5-dimethylthiazol-2-yl)-5-(3-carboxymethoxyphenyl)-2-(4-sulfophenyl)-2H-tetrazolium; CellTiter®96 Reagent, Promega) uptake assay was then employed to measure cell viability using the same assay plate, and the viability data was used to calculate compound cytotoxicity (CC$_{50}$). The Selectivity Index was calculated as CC$_{50}$/EC$_{50}$.

Conclusion: The test article was found to be potently active against HBV with a high selectivity index indicating high antiviral activity and low toxicity.

| Test article | EC$_{50}$ (µM) | CC$_{50}$ (µM) | Selectivity Index |
|---|---|---|---|
| ((((((R)-1-(6-amino-9H-purin-9-yl)propan-2-yl)oxy)methyl)(phenoxy)phosphoryl) oxy)methyl pivalate fumarate | 0.08 | >100 | >1250 |

3. In Vitro Efficacy of ((((((R)-1-(6-amino-9H-purin-9-yl)propan-2-yl) oxy)methyl)(phenoxy)phosphoryl) oxy)methyl Pivalate Fumarate Against HCV Using HCV Replicon Assay The subgenomic HCV replicons of genotype 1a (H77 strain), 1b (Coni strain), and 2a (JFH-1 strain), which are Huh7 human hepatoma cell lines that contains an HCV replicon were used.

The HCV replicon antiviral evaluation assay examines the effects of compounds at six serial dilutions. Human interferon alpha-2b (rIFNα-2b) and/or Sofosbuvir were included in each run as a positive control compound.

Briefly, the replicon cells were plated at 5,000 cells/well into 96-well plates that were dedicated for the analysis of cell numbers (cytotoxicity) or antiviral activity. On the following day, samples were diluted with assay media and added to the appropriate wells. Cells were processed 72 hours later when the cells were still sub-confluent. For the luciferase endpoint assay, HCV replicon levels were assessed as replicon-derived Luc activity. The concentration of drug that reduces cell viability was assessed by the fluorometric CytoTox-1 cell proliferation assay (Promega), (expressed as cell numbers). For the qRT-PCR/TaqMan assay, total RNA was extracted from the replicon cells using RNeasy 96 kit (Qiagen) according to the manufacturer's protocol. Real-time RTPCR/TaqMan assays was performed to measure copy numbers of the replicon RNA and cellular ribosomal RNA. Where applicable $EC_{50}$ (concentration inhibiting HCV replicon by 50%), $CC_{50}$ (concentration decreasing cell viability by 50%), and SI (selectivity indices: $CC_{50}/EC_{50}$) values were derived.

Conclusion: The test article was found to be active against HCV with a high selectivity index indicating high antiviral activity and low toxicity.

| Test article | $EC_{50}$ (μM) | $CC_{50}$ (μM) | Selectivity Index |
|---|---|---|---|
| ((((((R)-1-(6-amino-9H-purin-9-yl)propan-2-yl)oxy)methyl)(phenoxy)phosphoryl) oxy)methyl pivalate fumarate | 8.38 | 50.1 | 5.98 |

4. In Vitro Efficacy of ((((((R)-1-(6-amino-9H-purin-9-yl)propan-2-yl) oxy)methyl)(phenoxy)phosphoryl) oxy)methyl Pivalate Fumarate Against HIV-1 in Combination with 11 FDA Approved Drugs The anti-HIV-1 activity and cytotoxicity of ((((((R)-1-(6-amino-9H-purin-9-yl) propan-2-yl)oxy)methyl)(phenoxy)phosphoryl) oxy)methyl pivalate fumarate in two-drug combination studies with tenofovir, tenofovir alafenamide, emtricitabine, efavirenz, nevirapine, atazanavir, darunavir, cobicistat, raltegravir, dolutegravir, and elvitegravir was evaluated.

This two-drug combination analysis study was performed using the Prichard and Shipman MacSynergy II three dimensional model for statistical evaluation of combination anti-HIV assays. Using a standardized microtiter plate format, each combination assay was performed in MT4 cells acutely infected with HIV-1NL4-3.

MT4 cells (obtained from the NIH AIDS Research and Reference Reagent Program) were passaged in T-75 flasks prior to use in the antiviral assay. On the day preceding the assay, the cells were split 1:2 to assure they were in an exponential growth phase at the time of infection. Total cell and viability quantification was performed using a hemacytometer and trypan blue exclusion. Cells with greater than 95% cell viability were utilized in the assay. The cells were re-suspended in tissue culture medium and added to the drug-containing microtiter plates in a volume of 110 μL and at a seeding density of $5.0 \times 10^3$ cells/well.

A checkerboard plate format was used to test five concentrations of drug A (i.e., tenofovir, tenofovir alafenamide, emtricitabine, efavirenz, nevirapine, atazanavir, darunavir, cobicistat, raltegravir, dolutegravir, and elvitegravir) in all possible combinations with eight concentrations of drug B ((((((R)-1-(6-amino-9H-purin-9-yl)propan-2-yl)oxy) methyl) (phenoxy)phosphoryl) oxy)methyl pivalate fumarate). Combination antiviral efficacy was evaluated on three identical assay plates (i.e., triplicate measurements) that included cell control wells (cells only) and virus control wells (cells plus virus). Combination cytotoxicity was evaluated in parallel on two identical assay plates (i.e., duplicate measurements) that included cell control wells.

Following are the results from the antiviral testing of ((((((R)-1-(6-amino-9H-purin-9-yl) propan-2-yl)oxy) methyl) (phenoxy)phosphoryl) oxy)methyl pivalate fumarate) against HIV-1NL4-3 in infected (antiviral) and cytotoxicity testing in uninfected (cytotoxicity) MT4 cells in two-drug combination assays with tenofovir, tenofovir alafenamide, emtricitabine, efavirenz, nevirapine, atazanavir, darunavir, cobicistat, raltegravir, dolutegravir, and elvitegravir.

| Compound | Antiviral Activity Synergy/Antagonism volume | Cytotoxicity | Interpretation Antiviral | Cytotoxicity |
|---|---|---|---|---|
| Tenofovir | 79.0/−7.08 | 0/0 | Slightly synergistic/Additive | Additive |
| TAF | 41.2/−47.1 | 0/0 | Additive | Additive |
| Emtricitabine | 98.8/−8.75 | 0/−1.72 | Slightly synergistic/Additive | Additive |
| Efavirenz | 79.0/−5.92 | 0/−60.8 | Slightly synergistic/Additive | Additive/Slightly Antagonistic |
| Nevirapine | 47.6/−9.09 | 0/−0.97 | Additive | Additive |
| Atazanavir | 39.1/−3.50 | 16.3/−8.91 | Additive | Additive |
| Darunavir | 188/−36.5 | 0/−20.61 | Highly synergistic/Additive | Additive |
| Cobicistat | 0/−6.12 | 0/0 | Additive | Additive |
| Raltegravir | 1.61/−2.72 | 0/−4.70 | Additive | Additive |
| Dolutegravir | 17.9/−4.46 | 0/0 | Additive | Additive |
| Elvitegravir | 67.3/0 | 0/0 | Slightly synergistic/Additive | Additive |

Following are results from the antiviral and cytotoxicity testing of the "positive antagonism control" (stavudine/ribavirin) against HIV-1NL4-3 in MT4 cells.

| Stavudine + Ribavirin combination synergy/antagonism volumes (μM² %) | | | |
|---|---|---|---|
| Setup | Antiviral | Cytotoxicity | Interpretation |
| #1 | 71.8/−198 | 0.65/−31.4 | Antiviral: Highly antagonistic at |
| #2 | 23.1/−391 | 4.20/−2.93 | expected concentrations |
| Mean | 47.1/−294 | 2.42/−17.2 | Cytotoxicity: Additive |

We claim:

1. A pharmaceutical composition comprising ((((((R)-1-(6-amino-9H-purin-9-yl)propan-2-yl)oxy)methyl)(phenoxy)phosphoryl)oxy)methyl pivalate in the form of a fumarate salt or a pharmaceutically acceptable derivative thereof in an amount from about 2% to about 80% of the composition, one or more pharmaceutically acceptable excipients, and a therapeutic agent selected from the group consisting of: emtricitabine, efavirenz, nevirapine, darunavir, atazanavir, cobicistat, dolutegravir, elvitegravir, raltegravir, and any combination thereof.

2. The pharmaceutical composition according to claim 1, wherein the one or more pharmaceutically acceptable excipients are selected from carriers, diluents, fillers, binders, lubricants, glidants, disintegrants, bulking agents, flavorants or any combination thereof.

3. The pharmaceutical composition according to claim 1, wherein the composition is administered by oral route, topical route, rectal route, parenteral route or vaginal route.

4. The pharmaceutical composition according to claim 1, wherein the composition is in the form of an ingestible tablets, dispersible tablets, buccal tablets, troches, capsules, elixirs, solutions, suspensions, syrups, wafers, self-emulsifying drug delivery system (SEDDS), self-microemulsifying drug delivery system (SMEDDS), topical ointment, cream, gel, lozenges, ointment, suppository, vaginal ring, implant, spray foam, injectables, or in the form of a kit.

5. The pharmaceutical composition according to claim 1, wherein the ((((((R)-1-(6-amino-9H-purin-9-yl)propan-2-yl)oxy)methyl)(phenoxy)phosphoryl)oxy)methyl pivalate or the pharmaceutically acceptable derivative thereof has an average particle size less than 2000 nm.

6. The pharmaceutical composition according to claim 1, wherein the ((((((R)-1-(6-amino-9H-purin-9-yl)propan-2-yl)oxy)methyl)(phenoxy)phosphoryl)oxy)methyl pivalate or the pharmaceutically acceptable derivative thereof has an average particle size less than 250 nm.

7. The pharmaceutical composition according to claim 1, further comprising an additional therapeutic agent selected from the group consisting of nucleoside reverse transcription inhibitors (NRTIs), non-nucleoside reverse transcriptase inhibitors (NNRTIs), protease inhibitors (PIS), integrase inhibitors, CCR5 inhibitors, fusion inhibitors and maturation inhibitors (MIs) or any combination thereof.

8. The pharmaceutical composition of claim 1, further comprising an additional therapeutic agent selected from the group consisting of: zidovudine, didanosine, stavudine, lamivudine, zalcitabine, abacavir sulphate, delavirdine, saquinavir, nelfinavir, amprenavir, lopinavir, enfuvirtide, rilpivirine or any combination thereof.

9. The pharmaceutical composition according to claim 1, further comprising an additional therapeutic agent selected from the group consisting of recombinant Human Interferon Alfa, nucleoside analogs, direct acting antivirals, NS3/4A protease inhibitors (PIs), nucleotide NS5B polymerase inhibitors, NS5A Inhibitors, non-nucleoside NS5B Polymerase Inhibitors, or any combination thereof.

10. The pharmaceutical composition of claim 9, wherein the additional therapeutic agent is selected from peginterferon, ribavirin, sofosbuvir, daclatasvir, velpatasvir, voxilapravir, boceprevir, telaprevir, simeprevir, dasabuvir, ledipasvir, ombitasvir, paritaprevir, elbasvir, grazoprevir, asunaprevir, beclabuvir or any combination thereof.

11. A method of treating diseases caused by retroviruses or hepatitis B viruses or hepatitis C virus in a patient in need of such treatment, the method comprising administering a pharmaceutical composition comprising from about 2% to about 80% of the composition of a therapeutically effective amount of ((((((R)-1-(6-amino-9H-purin-9-yl)propan-2-yl)oxy) methyl) (phenoxy) phosphoryl) oxy) methyl pivalate in the form of a fumarate salt or a pharmaceutically acceptable derivative thereof, one or more pharmaceutically acceptable excipients, and a therapeutic agent selected from the group consisting of: emtricitabine, efavirenz, nevirapine, darunavir, atazanavir, cobicistat, dolutegravir, elvitegravir, raltegravir, and any combination thereof.

12. The pharmaceutical composition of claim 9, wherein the recombinant Human Interferon Alfa comprises pegylated interferon alfa-2a or pegylated interferon alfa-2b.

13. The pharmaceutical composition of claim 9, wherein the nucleoside analogs comprise ribavirin.

14. The pharmaceutical composition of claim 9, wherein the direct acting antivirals comprise daclatasvir, boceprevir, or telaprevir.

15. The pharmaceutical composition of claim 9, wherein the NS3/4A protease inhibitors comprise simeprevir.

16. The pharmaceutical composition of claim 9, wherein the nucleotide NS5B polymerase inhibitors comprise sofosbuvir.

17. The pharmaceutical composition of claim 9, wherein NS5A Inhibitors comprise daclatasvir.

18. The pharmaceutical composition of claim 9, wherein non-nucleoside NS5B Polymerase Inhibitors comprise dasabuvir.

19. The pharmaceutical composition according to claim 1, wherein the therapeutic agent is present in an amount from about 25% to about 50% of the composition.

20. The pharmaceutical composition according to claim 19, wherein the (R)-1-(6-amino-9H-purin-9-yl)propan-2-yl)oxy)methyl)(phenoxy)phosphoryl)oxy)methyl pivalate or the pharmaceutically acceptable derivative thereof is present in an amount from about 2% to about 15% of the composition.

* * * * *